United States Patent [19]

Ottenbrite

[11] Patent Number: 4,895,915
[45] Date of Patent: Jan. 23, 1990

[54] BIS[4-(3,4-DIMETHYLENE-PYRROLIDYL)-PHENYL] METHANE

[75] Inventor: Raphael M. Ottenbrite, Midlothian, Va.

[73] Assignee: The United States of America as represented by the Administrator of the National Aeronautics and Space Administration, Washington, D.C.

[21] Appl. No.: 311,551

[22] Filed: Feb. 16, 1989

Related U.S. Application Data

[62] Division of Ser. No. 221,386, Jul. 19, 1988, Pat. No. 4,851,544.

[51] Int. Cl.$^4$ .............................................. C08G 73/10
[52] U.S. Cl. ..................................... 526/262; 528/322
[58] Field of Search ......................... 526/262; 528/322

[56] References Cited

U.S. PATENT DOCUMENTS 4,115,359  9/1978  Darms et al. ........................ 526/262
4,713,422  12/1987  Kaschig et al. ..................... 526/262
4,839,440  6/1989  Barthelemy ......................... 528/322

Primary Examiner—Harold D. Anderson
Assistant Examiner—T. Mosley
Attorney, Agent, or Firm—George F. Helfrich; Charles E. B. Glenn; John R. Manning

[57] ABSTRACT

A polyimide composition consisting essentially of recurring units having the following structural formula:

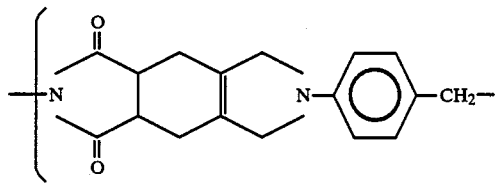

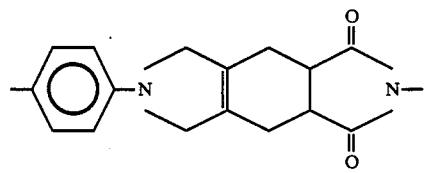

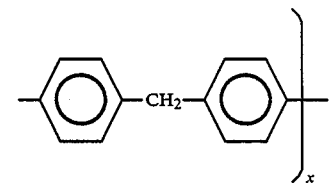

is produced by the copolymerization of a bismaleimide and bis[4-(3,4-dimethylenepyrrolidyl)phenyl] methane.

2 Claims, No Drawings

BIS[4-(3,4-DIMETHYLENE-PYRROLIDYL)PHENYL] METHANE

ORIGIN OF THE INVENTION

The invention described herein was made in the performance of work under a NASA Grant. In accordance with 35 USC 202, the grantee elected not to retain title.

This is a division of application Ser. No. 07/221,386, filed July 19, 1988.

BACKGROUND OF THE INVENTION

1. Field of the Invention

The present invention relates generally to high temperature polymeric materials. It relates particularly to linear aromatic polyimides prepared by copolymerizing a bismaleimide with bis[4-(3,4-dimethylenepyrrolidyl)-phenyl]methane.

2. Description of Related Art

A major goal in the field of high temperature polymers has been to prepare aromatic polyimides that can be easily fabricated with the required thermal and physical properties for aerospace applications. Recent research has been directed to achieve polyimides that are: (a) soluble in a common organic solvent; (b) melt-processable; and (c) thermally curable without the evolution of volatile by-products. See, for example: Mittal, K. L., "Polyimides: Synthesis, Characterization, and Applications", New York: Plenum Press, 1984; Cassidy, P. E., "Thermally Stable Polymers: Synthesis and Properties", New York: Marcel Dekker, Inc., 1980; and Hergenrother, P. and T. L. St. Clair, "Proceedings of Second International Conference on Polyimides", in Ellenville, New York, 1985.

The melt processability of polyimides can be enhanced by lowering the flow temperature, using synthetic techniques such as the incorporation of aryl-ether and meta-phenylene linkages in the polymer backbone.

A recent approach to obtain phenylated polyimides involves the Diels-Alder polymerization of phenylated biscyclopentadienones with bismaleimides (see Harris, H., "Polyimides: Synthesis, Characterization and Application", ed., K. L. Mittal, p. 3., New York: Plenum Press, 1984). The problem with this process is that during the reaction, carbon monoxide is produced subsequent to the Diels-Alder addition. Furthermore, at temperatures greater than 300° C., dehydrogenation, as well as other decomposition processes, occurs to yield a polymer with less solubility.

SUMMARY OF THE INVENTION

It is the primary object of the present invention to prepare high temperature polymeric materials, especially linear aromatic polyimides, which maintain their integrity and toughness during long exposure times at elevated temperatures.

According to the present invention, this object is achieved, and the attending benefits are obtained, by first providing the bis(exocyclodiene) bis[4-(3,4-dimethylenepyrrolidyl)phenyl]methane (identified as I in the general copolymerization equation below), which is a novel material formed from the monomer N-phenyl-3,4-dimethylenepyrrolidine. This bis-(exocyclodiene) undergoes Diels-Alder reaction with a bismaleimide (identified as II in the general copolymerization equation below), without the evolution of gaseous by-products, to form the aromatic polyimide (identified as III in the general copolymerization equation below), according to the present invention.

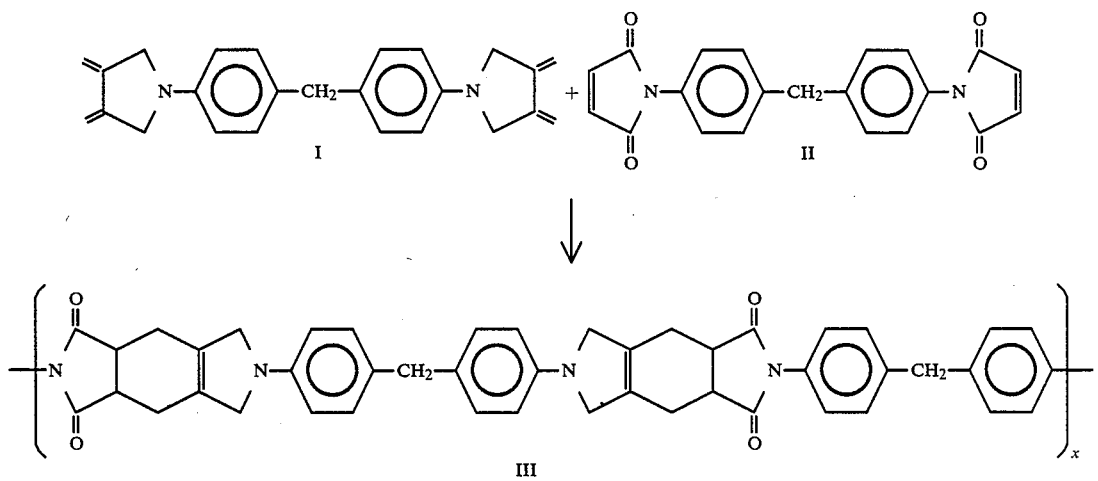

For a more complete understanding of the present invention, including its primary object and attending benefits, reference should be made to the Description of the Preferred embodiments, which is set forth below.

DESCRIPTION OF THE PREFERRED EMBODIMENTS

Synthesis of bis[4-(3,4-dimethylenepyrrolidyl)-phenyl]methane. The synthesis of phenyl methane was carried out by reacting 4,4'-methylenediamine arylenes with 2,3-bis(bromomethyl)-1,3-butadiene. During the reaction, the flask was covered with foil to avoid light catalyzed polymerization of the diene group of the starting material and product. $N_2$ sweep appeared to help retard the oxidation of the product. The product, bis(3,4-dimethylenepyrrolidyl)arylene, is very reactive and readily undergoes self-Diels-Alder addition. Since these dienes have poor solubility in organic solvents and poor stability, attempts to purify these monomers were not successful.

Self-Diels-Alder reaction of bis[4-(3,4-dimethylenepyrrolidyl)phenyl]methane. Dimerization which can result from a Diels-Alder reaction between two exocyclic dienes was observed in the case of N-phenyl-3,4-dimethylenepyrrolidine. To evaluate the stability of these bisdiene compounds, bis[4-(3,4-dimethylenepyrrolidyl)phenyl]methane (5% monomer in CDCl$_3$) was heated at 50° C. and followed by $^1$H NMR spectroscopy. After heating at 50° C. for seven hours, new multiplet signals appeared at δ2-3 region with decreasing endo protons of the exocyclic diene at δ5.5 region. It is estimated that the reaction ratio by self-Diels-Alder was 20-30% under model compound preparation conditions and 2-3% under conditions of polymerization based on the integration of the $^1$H NMR spectra.

Copolymerization of bis[4-(3,4-dimethylenepyrrolidyl)phenyl]methane with bis[4-(maleimidyl)-phenyl]methane. A polymer powder was prepared from the prepolymer solution which contained equimolar amounts of bis[4-(3,4-dimethylenepyrrolidyl)-phenyl]methane I and bismaleimide II in solution. After standing overnight, the prepolymer solution became a gel. The polymer gel was washed with chloroform and acetone, and then dried in vacuo.

Polymer film. Polymer films were prepared by casting the prepolymer solution onto a clean glass surface. The glass plates were held at room temperature overnight to allow the solvent to evaporate. The films were then heated at 120° C. for 12 hours to give transparent flexible polymer films. These films were heated another 12 hours at 150° C.

Observations. It was observed that bis[4-(3,4-dimethylenepyrrolidyl)phenyl]methane reacts very rapidly with bismaleimide by Diels-Alder addition. However, this reaction is slower in acidic solvents, such as trifluoroacetic acid, due to the protonation of the nitrogen in the pyrrolidine ring. The polymerization of bis[4-(3,4-dimethylenepyrrolidyl)phenyl]methane with bismaleimide was followed by $^1$H NMR spectroscopy. At 50° C. in trifluoroacetic acid, complete polymerization could be achieved within 48 hours. The polymerization yield was estimated to be 92% based on the integration of the $^1$H NMR spectrum.

The $^1$H NMR peak height decreases from the bisdiene protons and the polymer backbone proton area increases during the reaction. The new methylene protons on the central ring due to the Diels-Alder addition is consistent with the decreasing exocyclic diene peak. Consequently, it is considered that the Diels-Alder reaction is the predominant process in this polymerization. The inherent viscosity determined during the polymerization was plotted against the $^1$H NMR signal height due to the newly formed methylene protons. (See Drawing.) It appears that, after formation of oligomer dimers and trimers within the first three hours, the elongation of the polymer chain takes place as indicated by the increasing viscosity with time.

The Effect of Mole Ratio of Monomer on Film Properties. After determining the monomer concentration of bis[4-(3,4-dimethylenepyrrolidyl)phenyl]methane by $^1$H NMR spectrum, the bismaleimide comonomer was added to the solution to make the preopolymer solution. Polymer films were then prepared from this prepolymer solution. Shown in Table 1 below are the film properties which were found to depend on the mole ratio of both monomers. The addition of 20-30% less bismaleimide II then bisdiene I made good flexible films. This observation might be explained by the fact that the 20-30% of the bisdiene may be undergoing a self-Diels-Alder process as described earlier.

TABLE 1

THE EFFECT OF MOLE RATIO OF MONOMERS ON FILM PROPERTIES

| Mole Ratio (I) | Mole Ratio (II) | Solution Viscosity | Film Property |
| --- | --- | --- | --- |
| 1.0 | 1.0 | nonviscous | brittle |
| 1.0 | 0.9 | nonviscous | brittle |
| 1.0 | 0.8 | viscous → gel | flexible |
| 1.0 | 0.7 | viscous → gel | flexible |
| 1.0 | 0.6 | nonviscous | brittle |

Solubility. The original polymer film was insoluble in organic solvents, hot, concentrated sulfuric acid was used as a solvent for five different polymer films which had different curing temperatures after casting. See Table 2 below. The polymer films were treated at temperatures above 120° C. were not soluble in hot H$_2$SO$_4$. This decreased solubility may be due to a crosslinking reaction taking place in the polymer film after heating at high temperatures and/or oxidation of the pyrrolidine ring to the aromatic pyrrole.

TABLE 2

SOLUBILITY OF POLYMER FILM IN CONCENTRATED H$_2$SO$_4$

| Film Curing Temperature (°C.) | Film Solubility |
| --- | --- |
| 25 | partially soluble |
| 50 | partially soluble |
| 120 | insoluble |
| 160 | insoluble |
| 200 | insoluble |

Thermal Analysis. The thermal stability and decomposition temperature of the polymer films were analyzed by thermogravimetric analysis (TGA). The measurements were carried out in N$_2$ and in an air atmosphere, respectively. The polymer film was thermally stable with only 10% weight loss at 357° C., and 20% weight loss occurred at 413° C. in nitrogen. The thermal data of the polymer film are tabulated in Table 3 below. On the other hand, TGA plots in air showed different behavior. These two plateau regions in the TGA curve were observed. The second rapid weight loss occurred above 400° C. and was indicative of total decomposition of the polymer backbone. The first moderate weight loss occurred at a much lower temperature (239° C.).

TABLE 3

THERMAL PROPERTIES OF POLYMER FILM BY THERMOGRAVIMETIC ANALYSIS

| Atmosphere | T (°C.) 10% Weight Loss | T (°C.) 20% Weight Loss |
| --- | --- | --- |
| nitrogen | 357 | 413 |
| air | 239 | 385 |

The present invention has been described in detail with respect to certain preferred embodiments thereof. However, it is understood by those of skill in the art that variations in this detail may be made without any departure from the spirit and scope of the present invention, as defined in the hereto appended claims.

What is claimed is:

1. A polyimide composition consisting essentially of recurring units having the following structural formula:

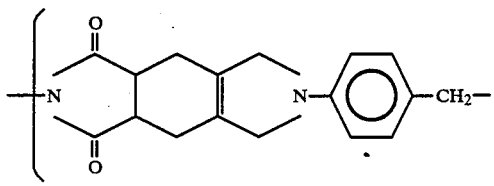
-continued
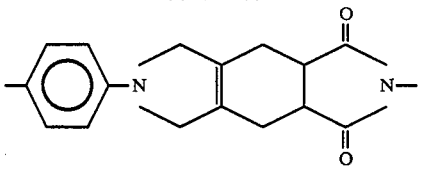
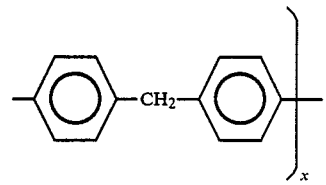
2. The polyimide of claim 2, which is prepared by the copolymerization of bis[4-(3,4-dimethylenepyrrolidyl)-phenyl]methane and bis[4-(maleimidyl)phenyl]methane.